United States Patent [19]

Sussman

[11] Patent Number: 4,690,276

[45] Date of Patent: Sep. 1, 1987

[54] CONTAINERS FOR COSMETIC SUNDRIES

[76] Inventor: Howard Sussman, 3101 NW. 25th Ave., Pompano Beach, Fla. 33069

[21] Appl. No.: 904,030

[22] Filed: Sep. 5, 1986

[51] Int. Cl.$^4$ ............... B65D 83/02; B65D 21/02
[52] U.S. Cl. ............... 206/36 X; 215/100 R; 215/1 C; 221/269
[58] Field of Search ............... 206/349, 361, 209, 504; 215/1 C, 3, 100 R; 221/247, 269, 248, 249, 229

[56] References Cited

U.S. PATENT DOCUMENTS

| | | | |
|---|---|---|---|
| 1,143,654 | 6/1915 | Smykal | 221/229 |
| 2,546,208 | 3/1951 | Barton | 215/1 C |
| 3,225,951 | 12/1965 | Poston et al. | 215/1 C |
| 3,362,556 | 1/1968 | Waldrum | 215/1 C |
| 3,712,497 | 1/1973 | Jones | 215/1 C |
| 3,768,685 | 10/1973 | Eckman | 215/100 R |
| 4,133,445 | 1/1979 | Mandelbaum | 206/504 X |

FOREIGN PATENT DOCUMENTS

| | | | |
|---|---|---|---|
| 2015044 | 9/1971 | Fed. Rep. of Germany | 221/247 |
| 2082546 | 3/1982 | United Kingdom | 221/247 |

Primary Examiner—William Price
Attorney, Agent, or Firm—Myron Amer

[57] ABSTRACT

A container having two vertical similarly shaped integrally connected sections each adapted to hold a different class of sundry. One of the containers has a movable bottom and an articulating link connecting the movable bottom to a lid so that the bottom is raisable on lifting of the lid.

7 Claims, 9 Drawing Figures

CONTAINERS FOR COSMETIC SUNDRIES

BACKGROUND OF THE INVENTION

The present invention relates to containers for cosmetic sundries and in particular to containers for storing and dispensing items such as cotton tipped swabs and cotton balls.

Among the criteria considered by the ultimate users of such containers is whether an individual container will allow the user to have quick and easy access to the stored items and whether the removal of single or individual items does not result in disarrangement of those remaining. Another criteria is to provide a container of small size, in which at least two sundry items may be stored, and which may be placed on a dressing table or countertop space, so that the contents may be readily accessible, without taking up an inordinately large area.

Amongst the cosmetic items often used and in need of containers to maintain them clean, fresh and unscattered over a dressing table are cotton pads and cotton tipped swabs. These particular items present considerable problems when concern for the foregoing criteria are considered. Namely, the tipped swabs, are light, stick-like objects which tend to adhere together at their tips and tend to roll and disburse helter-skelter when handled in their original box or container. Cotton pads or balls also stick together and have a tendency to flatten when handled. More significantly, these two items are difficult to store together, or even in proximity in an open container.

It is, therefore, the specific object of the present invention to provide a container for tipped cotton swabs and cotton balls which overcomes the aforementioned disadvantages and difficulties.

It is a specific object to provide a covered container for tipped cotton swabs which hold the swabs and which enable removal of one or more individual swabs without unduly interfering with the remaining swabs. It is also a specific object to provide a covered container for cotton balls which enable the user to have free access of the balls without unduly compressing them or subjecting the balls to dirt or unnecessary handling.

It is a material object of the present invention to provide a combined unitary container for tipped swabs and cotton balls which not only satisfies the foregoing objectives, but is also attractive, simple in ornamentation, and which takes up a relative small table top area.

These objectives, as well as other objects and advantages will be forthcoming from the following disclosure of the present invention.

SUMMARY OF THE INVENTION

According to the present invention a container is provided having two sections each adapted to hold a particular class of sundry articles. Each section is formed of a vertically oriented sleeve having an open top and removable lid. One of the sleeves is provided with a relatively fixed bottom wall, while the other sleeve is provided with a tray adapted to freely slide up and down in the sleeve. The tray is connected to the lid of its sleeve by an articularing connection whereby on lifting of the lid the tray is elevated.

The articulating connection is preferably an elongated flat bar having a trunion formed at each end and both the tray and the lid are formed with a clevis receiving the trunion. In this manner, both the tray and the lid are relatively pivotable with respect to the flat bar and with each other. The tray is thus held in elevated position by pivoting the lid over the open top of the sleeve.

Preferably, both sleeves are oval in cross section, the sleeve having the removable tray being taller than the other sleeve which not only is shorter, but has larger major and minor axes.

Full details of the present invention are set forth in the following description and illustrated in the accompanying drawings.

DESCRIPTION OF THE PREFERRED EMBODIMENTS

The present invention is shown as being specifically designed for use with cotton tipped swabs and cotton balls which are among the most common cosmetic sundries used. They also conveniently aid in explaining both the functional and structural advantages of the present invention. It will be understood, however, that the container may be used with other products as well.

Figure 8:
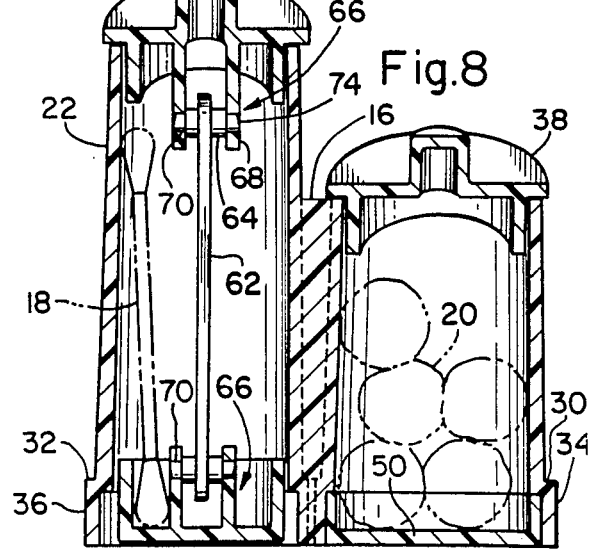
FIG. 8 is a sectional view taken along line 8—8 of FIG. 2.

The container of the present invention as generally shown in FIGS. 1 to 5 is designated by the numeral 10 and comprises two sections 12 and 14 connected by an integral web 16. One of the sections, namely section 14, is taller than the other and is particularly adapted (as illustrated in FIG. 8) to hold elongated stick-like cotton tipped swabs 18 while the other section (namely section 12) is somewhat shorter and is adapted to hold cotton balls 20.

As seen in detail in FIGS. 5 to 8, the containers 12 and 14 are formed as vertically oriented sleeves 22 and 24 respectively, each having an oval or similar transverse cross-sectional shape and which have their minor axes aligned and their major axes parallel. Each of the sleeves 22 and 24 is open at its upper end 26 and 28 respectively and have smooth, uniform interior and exterior surfaces. Along the bottoms each of the sleeves are stepped outwardly from a shoulder 30 and 32 to provide radially enlarged peripheral bands 34 and 36 respectively, both terminating in the same diametric plane to provide a stable horizontal footing for the containert as a whole. The top ends 26 and 28 are each cut at an angle to the central vertical axis so that the ends lie in separate but parallel planes inclined with respect to the horizontal. While the taller sleeve 28 is narrower in both its major and minor cross sectional axes than that of the shorter sleeve 26, it is contemplated that they can be otherwise similarly shaped.

Figure 7:
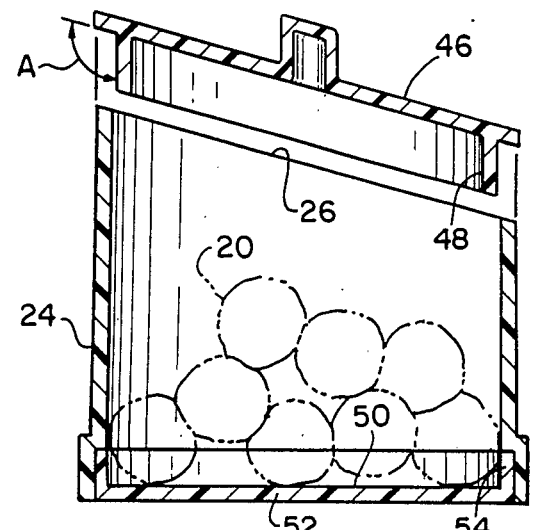
FIG. 7 is a sectional view along line 7—7 of FIG. 2; showing the section for cotton swabs.
Figure 4:
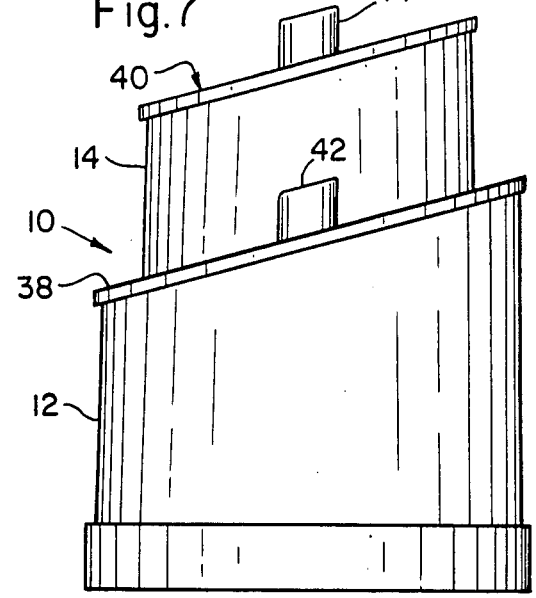
FIG. 4 is a right side elevated view thereof.

Each of the top ends 26 and 28 are provided with lids 38 and 40 having central knobs 42 and 44, respectively and are substantially of identical construction, each comprising a plate-like disk 46 conforming in shape to and somewhat larger to that of the respective sleeve, so as to seat fully over the top edge 26 or 28. Each plate 46 is provided with a depending pheripheral skirt 48 also conforming in shape to the respective sleeve, so as to fit closely, but slidably therein. As seen in FIG. 7 the peripheral skirt 48 is set at an angle A to the plate 46 so that the plate 46 is itself inclined angularly to the vertical axis, conforming so the inclined plane of the top edge 26 and 28 repsectively.

The shorter container 22 is provided with a bottom tray 50 which comprises a bottom wall 52 and an integrally formed upwardly extending peripheral wall 54. The tray 50 generally conforms to the shape of the sleeve 22, so as to fit comfortably therein, and the peripheral upstanding wall 54 has a height substantially equal to that of the band 34 at the bottom of the sleeve 22. Preferably, the tray 50 is glued or heat sealed to the interior surface of the sleeve 22 so as to be permanently attached thereto. It may, however, be removably set in the sleeve by providing on its exterior surface a plurality of interference ridges preferably in line in the major and minor axes, whereby a force-fit may be created between the ridges and the inner surface of the sleeve.

The taller container section 14 is provided with a similarly shaped tray, generally designated by the numeral 56 in that it is formed of a bottom wall 58 and a peripheral side wall 60 conforming in overall shape to that of the sleeve 14. However, the overall major and minor axes of the tray 56 are somewhat smaller than those of the sleeve 24 so that it is easily movable within the sleeve. To insure smoothness of such movement the peripheral side wall 60 is somewhat taller than the height of the band 36 forming the bottom of the sleeve 24. The tray 56 is retained in the sleeve 24 by being suspended from its cover 40 by an articulated connection comprising an elongated flat bar link 62. Integrally formed at each of the ends of the bar link 62 is a trunion 64 which respectively fit into clevises 66; one of the clevises 66 being affixed on the inner surface of the bottom wall 58 of the tray 56 and the other being affixed to the plate 46 of the cover 40. The clevises 66 are preferably intergrally formed with the respective tray bottom wall 58 and cover plate 46 and each comprises a pair of posts 68 having aligned holes 70 adapted to receiving the stub axle 72 of the trunion 64. The stub axles 72 have their ends 74 champhered so as to permit the snap fitting of the stub axles within the clevis holes. The peripheral wall 60 of the tray 56 is provided with a pair of notches 76 to allow for withdrawal of pins of the molding die that form the holes 70 in the posts 68.

Figure 1:
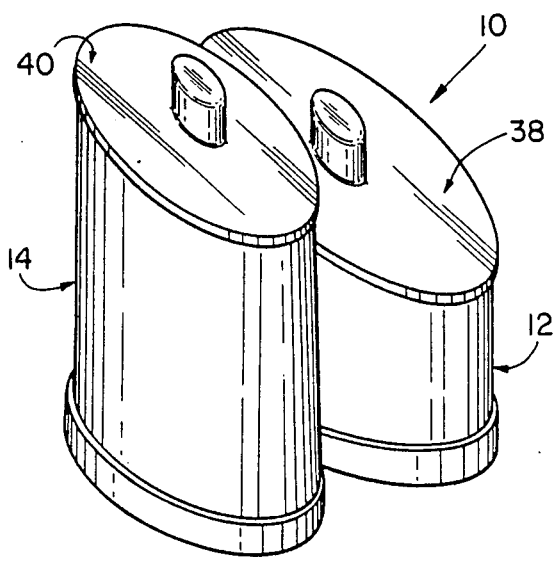
FIG. 1 is an isometric view of the container of the present invention having separate sections for tipped swabs and cotton pads.
Figure 2:
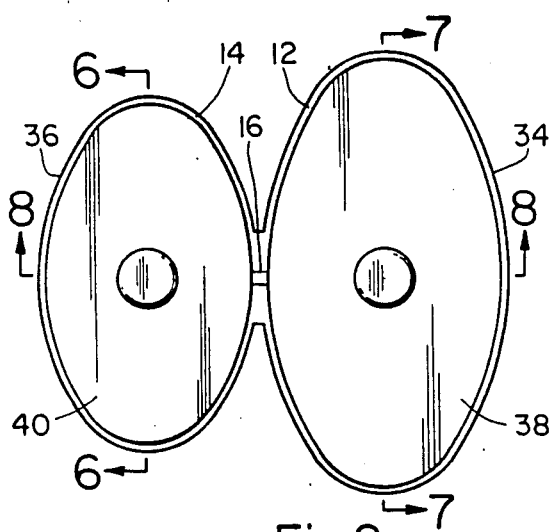
FIG. 2 is a top plan view thereof.
Figure 3:
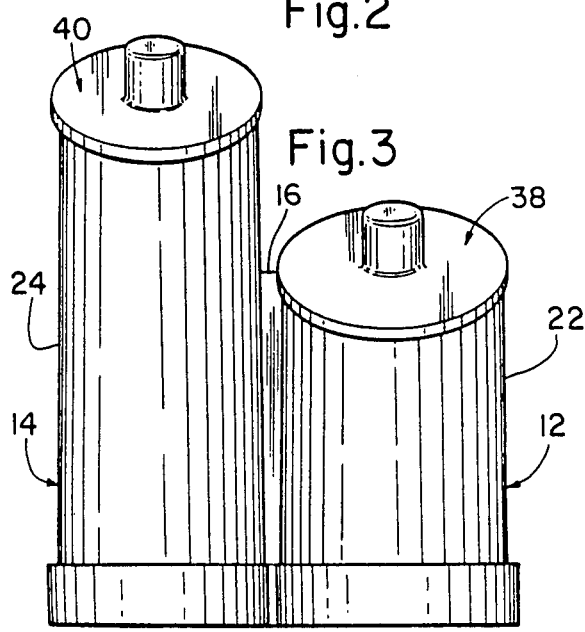
FIG. 3 is a front elevational view thereof.
Figure 5:
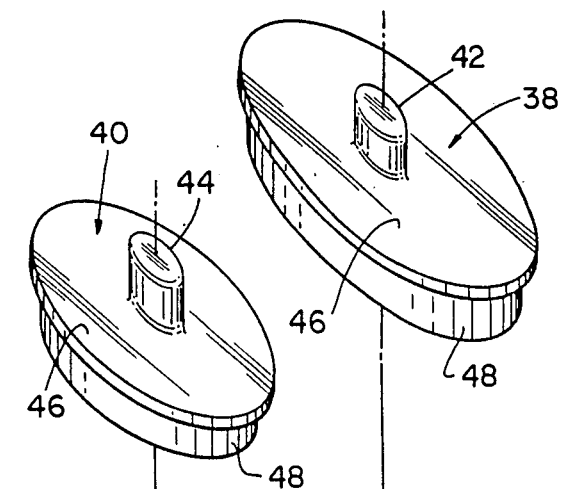
FIG. 5 is an exploded view of the container of the present invention showing its various parts.
Figure 5:
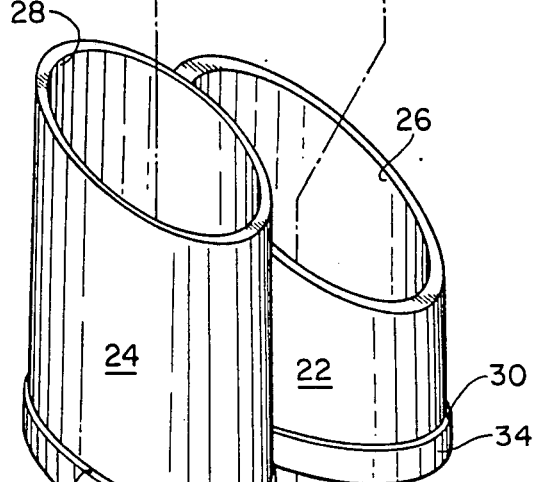
Figure 5:
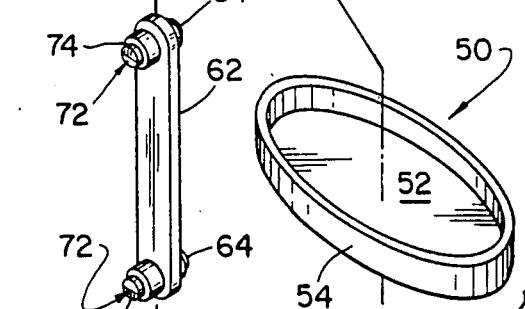
Figure 5:
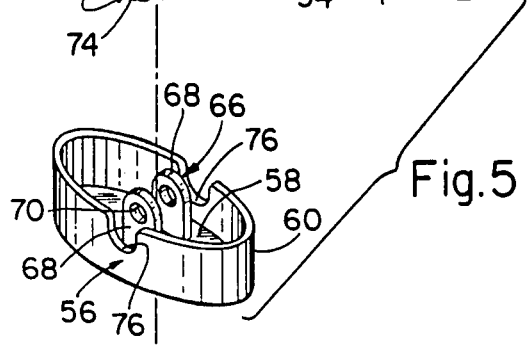
Figure 6A:
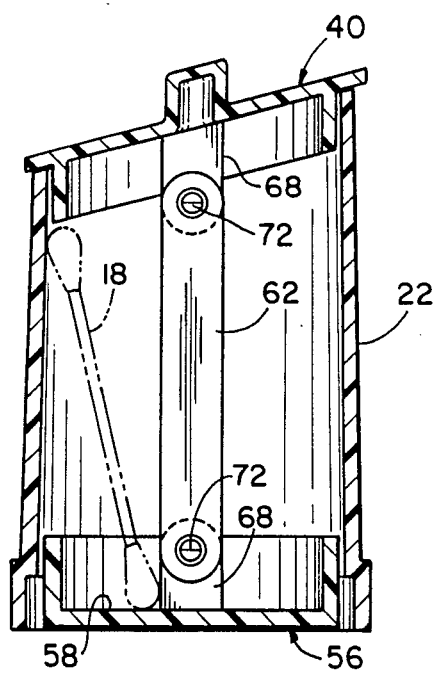
FIG. 6a is a sectional view taken along line 6—6 of FIG. 2 with the container lid of the tipped swab section in closed condition.
Figure 6B:
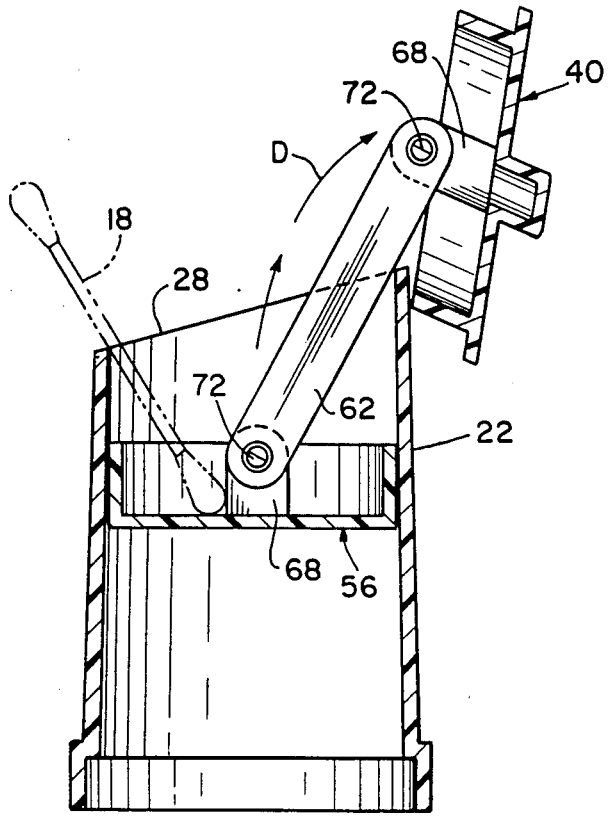
FIG. 6b is a view similar to that of FIG. 6a with the cover lifted to provide access to the container.

As seen in FIGS. 6a and 8, when the cover is placed on the container section 14 to thereby close it, the link 62 hangs vertically, suspending the tray 56 so that it descends to the bottom of the sleeve 24, thereby permitting the tipped swabs 16 to be fully enclosed within the sleeve and the lid 40 resisting on the sleeve 24. However, by merely tilting the lid 40 upwards and backwards in the direction of arrow D, (FIG. 6b) over the highest point of the upper end 28 of the sleeve 24, the tray 56 is elevated a sufficient distance above the bottom to raise the swabs 16 above the lower portion of the inclined edge, so that they are readily accessible to the user. In this manner, single swabs may be removed without handling the remaining swabs contained within the sleeve. Of course, when the user wishes to refill the sleeve with additional swabs, the entire cover and its pivotally attached tray can be manually lifted a greater distance, rendering the tray more accessible to the user.

Preferably, the material from which the container as a whole is formed is of plastic, such as Lucite, or any one of the other decorative plastic materials currently available. As a result, the sleeves and the connecting webs may be molded together in a unitary manner. In doing so, it is preferred to provide the draft angle of the sleeves 22 and 24 be tapered to be somewhat larger at the upper end of the sleeve so as to insure the insertion of the trays from that end.

It will be appreciated from the foregoing, that the various objects and advantages enumerated earlier, as well as described herein, have been fully met. Various changes and modifications have been suggested and others will be obvious to those skilled in the art. Accordingly, it is intended that the description be taken as illustrative only of the invention and not as limiting its scope.

What is claimed is:

1. A container for cosmetic sundries having two integrally connected sections, each adapted to hold a particular class of sundry articles, each section comprising a vertically oriented sleeve having an open top and a removable lid, one of said sleeves having a relatively fixed bottom wall and the other one of said sleeves having a bottom tray movable within said other sleeve and an articulating connection between said bottom tray and the associated lid to present the articles held in said other sleeve above the top thereof, said articulating connection comprising a flat bar having a trunion at each end and said tray and lid have clevis means for pivotaly receiving said trunion, said tray and lid being relatively movable with respect to said bar and to each other.

2. The container according to claim 1, wherein said bar has a length which upon lifting of said lid and tilting of said lid over the top of the associated sleeve suspends said tray between the top and bottom ends of said sleeve.

3. The container according to claim 1, wherein said clevis means comprise a pair of posts integrally formed with the lid and tray respectively, each pair of posts having aligned holes for receiving the ends of said trunion, the ends of said trunion being champhered to snap fit into said holes.

4. The container according to claim 1, wherein the tops of said sleeves are inclined to the horizontal in parallel planes.

5. The container according to claim 4, wherein said sleeves are oval in cross section and are connected by a web aligned with the minor axis of said sleeves.

6. The container according to claim 5, wherein said one sleeve has minor and major axes larger than said other sleeve and is shorter than said other sleeve.

7. The container according to claim 4, wherein each of said lids comprises a plate conformingly shaped and coextensive with the top of the associated sleeve, said plate having a peripheral skirt depending therefrom conformingly shaped and adapted to fit within the top of said sleeve, said skirt being integrally secured to said plate at an angle to said plate conforming to the angle of incline of the top of its associated sleeve.

* * * * *